United States Patent
Frey et al.

(10) Patent No.: US 8,286,970 B2
(45) Date of Patent: Oct. 16, 2012

(54) DEVICE FOR AFFIXING TO CYLINDRICAL COMPONENTS OF MEDICAL INSTRUMENTS

(75) Inventors: Sebastian Frey, Villingen-Schwenningen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1301 days.

(21) Appl. No.: 11/943,660

(22) Filed: Nov. 21, 2007

(65) Prior Publication Data
US 2008/0122148 A1    May 29, 2008

(30) Foreign Application Priority Data
Nov. 23, 2006    (DE) .......................... 10 2006 055 172

(51) Int. Cl.
*B23B 31/20*    (2006.01)
(52) U.S. Cl. .............................. 279/43.4; 279/51; 279/95
(58) Field of Classification Search ................ 279/20.1, 279/43, 43.1, 43.2, 43.4, 51, 89, 93–96, 46.3; *B23B 31/20*
See application file for complete search history.

(56) References Cited

U.S. PATENT DOCUMENTS

| | | | | |
|---|---|---|---|---|
| 985,536 | A * | 2/1911 | Muehlmatt | 279/51 |
| 2,436,848 | A * | 3/1948 | Benjamin et al. | 279/50 |
| 2,839,953 | A * | 6/1958 | Hanger | 408/72 R |
| 5,456,673 | A | 10/1995 | Ziegler et al. | |
| 5,716,369 | A | 2/1998 | Riza | |
| 6,228,059 | B1 | 5/2001 | Astarita | |
| 6,880,832 | B2 * | 4/2005 | DeRosa | 279/44 |
| 6,908,264 | B1 * | 6/2005 | Gundy | 408/204 |
| D606,194 | S * | 12/2009 | Frey et al. | D24/147 |
| D610,681 | S * | 2/2010 | Frey et al. | D24/140 |
| D617,458 | S * | 6/2010 | Frey | D24/138 |
| D622,846 | S * | 8/2010 | Frey | D24/138 |

FOREIGN PATENT DOCUMENTS

| | | |
|---|---|---|
| DE | 199 16 088 | 10/2000 |
| DE | 10 2004 043 982 | 3/2006 |
| EP | 1832220 A2 | 9/2007 |
| WO | 2006132955 A2 | 12/2006 |

OTHER PUBLICATIONS

European Search Report; EP 07 02 2292; May 20, 2009; 2 pages.
German Search Report, Jul. 30, 2007, 4 pages.

* cited by examiner

*Primary Examiner* — Eric A Gates
(74) *Attorney, Agent, or Firm* — St. Onge Steward Johnston & Reens LLC

(57) ABSTRACT

The invention relates to a device for affixing to cylindrical components of medical instruments, for instance an instrumental shaft, having at least one intake part that can be mounted on the cylindrical component and can be affixed to the cylindrical component, wherein a sleeve-shaped collet chuck that essentially coaxially surrounds the cylindrical component is positioned in the intake part and whose inner diameter can be displaced between a span that can slide along the cylindrical component and a span that is in form-locking contiguity on the cylindrical component. To allow for a stationary clamping on the one hand and ensure a non-harmful clamping of the cylindrical component on the other hand, it is proposed with the invention that the inner diameter of the collet chuck can be displaced by a slider that can slide essentially diagonally to the cylindrical component and is mounted so that it can slide in the housing of the intake part.

13 Claims, 2 Drawing Sheets

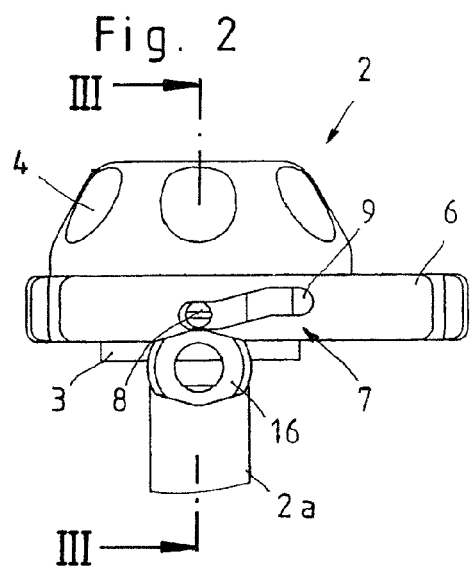
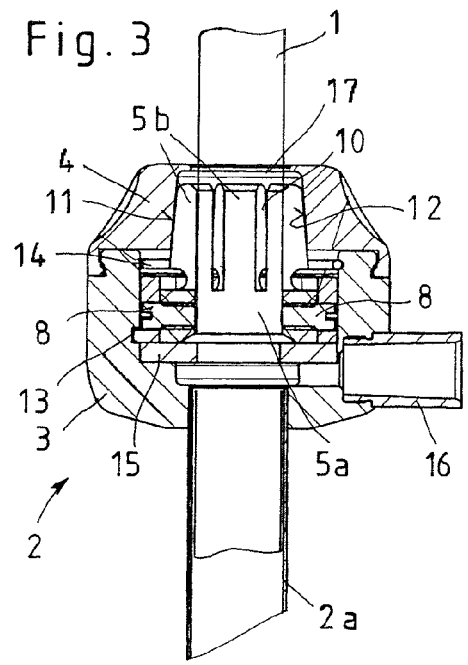
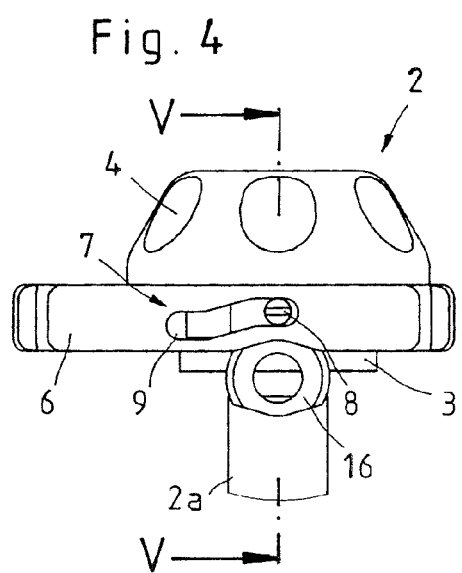
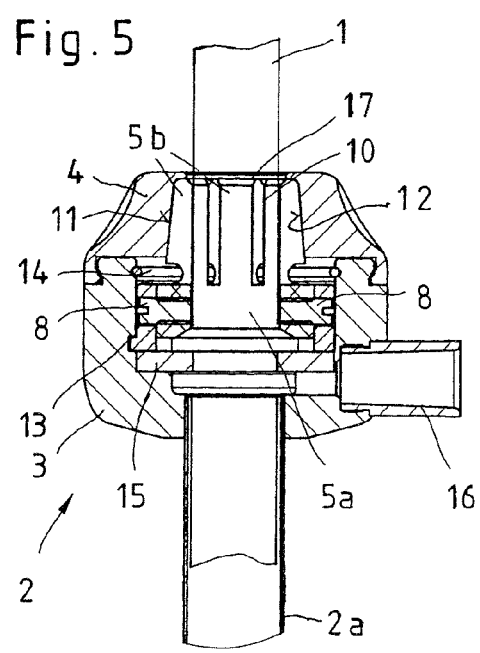

DEVICE FOR AFFIXING TO CYLINDRICAL COMPONENTS OF MEDICAL INSTRUMENTS

CROSS-REFERENCE TO RELATED APPLICATIONS

The present application claims priority of German patent application No. 10 2006 055 172.9 filed on Nov. 23, 2006, the content of which is incorporated herein by reference.

FIELD OF THE INVENTION

The invention relates to a device for affixing to cylindrical components of medical instruments, for instance an instrument shaft, having at least one intake part that can be positioned on the cylindrical component and can be affixed to the cylindrical component, wherein there is positioned in the intake part a sleeve-shaped collet chuck that essentially coaxially surrounds the cylindrical component and whose inner diameter can be displaced between a span that can move along the cylindrical component and a span that is essentially in form-locking contiguity with the cylindrical component.

BACKGROUND OF THE INVENTION

Clamping devices of this type are used in order to affix other components such as handgrips, guides, or medical instruments onto a medical instrument. The configuration of the affixing device as a clamping device has become standard in the art because this configuration as a rule is easy to operate and can be used reversibly. The disadvantage in clamping devices known in the art is that, because of the configuration of the clamping mechanism, there is a risk that the cylindrical component to which the clamping device is to be attached will be damaged. This risk is especially present when the cylindrical component is an optic system or the shaft tube of the lens system.

A generic clamping device is known, for instance, from DE 199 16 088 A1. With this known clamping device, the instrument that is to be affixed is secured by two shell halves that surround the cylindrical shaft of the instrument and can be compressed together by means of an eccentric tappet in such a way that the shell halves clamp onto the instrument shaft. This clamping mechanism has proven itself in the art, but the actuation of the eccentric tappet lever can require considerable force, in particular with large shaft diameters.

It is consequently the object of the invention to produce a clamping device of the aforementioned type, which in addition to being simple to operate, both makes possible a securely stationary clamping and ensures protective clamping of the cylindrical component.

SUMMARY OF THE INVENTION

The fulfillment of this object, according to the invention, is characterized in that the inside diameter of the collet chuck can be displaced by means of a slider positioned to slide essentially diagonally to the cylindrical component in the housing of the intake part.

The use of this slider for reversible transfer of the collet chuck from the open to the clamping position constitutes an especially simple and quickly managed displacement possibility for affixing a component in secure stationary manner, secure against rotation, on the cylindrical component.

By configuring the clamping element of the intake part as a sleeve-shaped collet chuck that surrounds the cylindrical component essentially coaxially, it becomes possible to distribute the clamping force exerted on the cylindrical component by configuring an axially extending surface pressure over the entire periphery of the cylindrical component in such a way that no inward-pressing or tapering local clamping occurs.

To facilitate installation of the inventive clamping device and to ensure that the slider is always inserted in the housing in the correct position, the invention foresees mutually corresponding guide and positioning elements on the slider and on the housing of the intake part.

According to a preferred embodiment of the invention it is proposed that for reversible transfer of the collet chuck from open to clamping position, the collet chuck and slider are in active connection to one another by way of a mortise-and-tenon control, whereby the mortise-and-tenon control preferably consists of at least one control pin that is mounted on the collet chuck and engages in a guide track configured in the slider. Mortise-and-tenon controls are characterized in that, in addition to simplicity in manufacture, they ensure a reliable switching of the components that they propel.

According to the invention, the guide track of the slider is configured in such a way that a height adjustment is configured in the guide track configured in the slider, viewed in the axial direction of the cylindrical component.

It is further proposed with the invention that the collet chuck should be mounted so that it can slide axially in the housing of the intake part in order to displace the collet chuck between its two end positions, namely the open position which releases the cylindrical component and the clamping position that clamps the cylindrical component.

According to a preferred embodiment of the invention it is proposed that the clamping effect of the collet chuck is produced when the a cone is configured on the collet chuck that can be brought into active connection with a counter-cone configured in the housing of the intake part, so that the collet chuck preferably can be slid axially by means of the at least one guide mortise mounted in the guide track of the slider in such a way that the cone of the collet chuck can be displaced between a position contiguous with the counter-cone of the housing and a position that releases the counter-cone of the housing.

The configuration of the components that produce the actual clamping effect as cone and counter-cone constitutes an embodiment that is simple to manufacture and to operate. The collet chuck, which includes the cone, is pressed against the counter-cone by the mortise-and-tenon control upon closing of the clamping connection and it is drawn away from the counter-cone upon releasing the clamping connection.

With a practical embodiment of the invention it is further proposed that the counter-cone should be configured on the inside of a cover cap that can be placed on the housing of the intake part.

To ensure that, when the cover cap is removed, the slider cannot fall out of the housing of the intake part, according to the invention a securing element, in particular a snap ring, is positioned in the housing of the intake part for lateral securing of the slider.

It is finally proposed with the invention that at least one insulation element should be positioned in the housing of the insertion piece in order to insulate the washing circuit of the medical instrument.

Further characteristics and advantages of the invention can be seen from the appended illustrations in which an embodiment of an inventive device for affixing to cylindrical components of medical instruments is depicted in exemplary manner, without restricting the invention to said embodiment.

BRIEF DESCRIPTION OF THE DRAWINGS

FIG. 2 shows a side view of the clamping device of FIG. 1, depicting the open position.

FIG. 3 shows a sectional view along the line III-III from FIG. 2.

FIG. 4 shows a side view of the clamping device of FIG. 2, but depicting the clamping position.

FIG. 5 shows a sectional view along the line V-V of FIG. 4.

DETAILED DESCRIPTION OF THE INVENTION

Figure 1:
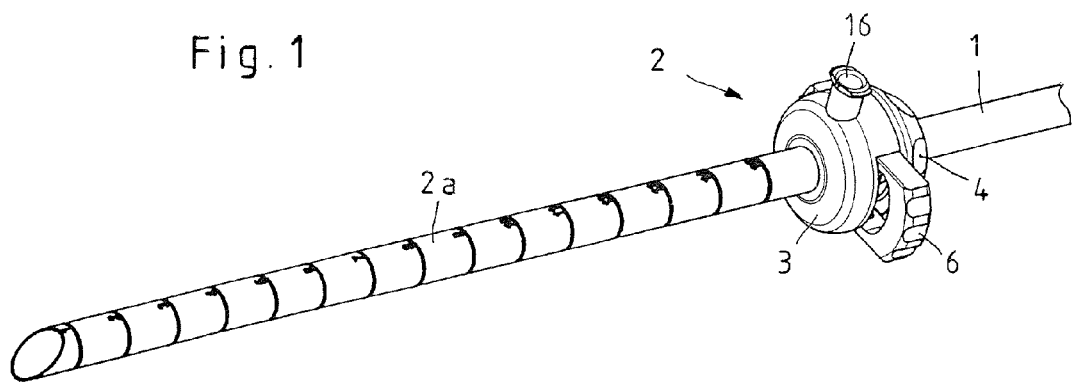
FIG. 1 shows a perspective side view of an inventive device for affixing to cylindrical components of medical instruments which is secured to an instrument shaft.

The device illustrated in FIGS. 1 through 7 for affixing medical instruments onto cylindrical components 1, such as instrument shafts or optical systems of endoscopic instruments, consists essentially of an intake part 2 that can be mounted on the cylindrical component 1 and in which the actual clamping mechanism is positioned. The intake part 2 consists, as can be seen in particular from FIGS. 3 and 5, of a housing 3 that can be closed by means of a cover cap 4.

Claming devices of this type are used in order to secure other components, such as handgrips, guides, or even medical instruments, to a medical instrument.

In the illustrated embodiment, the intake part 2 includes an applied outer tube 2a for inserting the cylindrical component 1 that is to be affixed. It is also possible, of course, to configure the intake part without this outer tube 2a, so that the cylindrical component 1 that is to be affixed extends in the longitudinal direction through the intake part 2.

Figure 6:
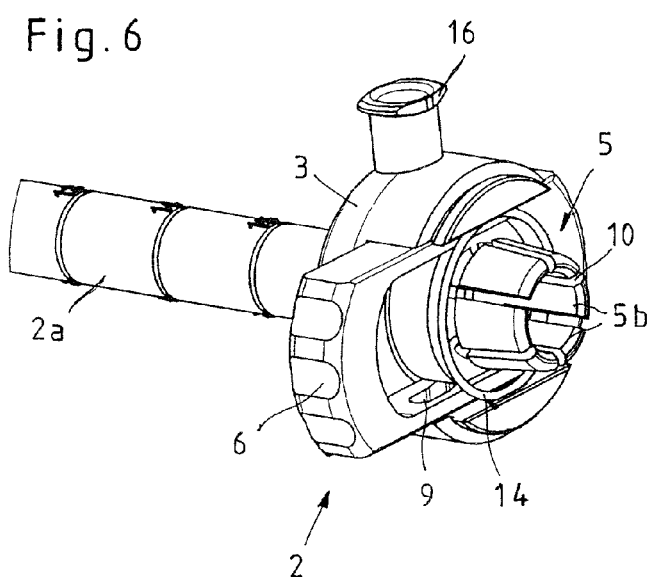
FIG. 6 shows a perspective front view of the depiction in FIG. 1, but without the front cover cap.

As can be seen in particular from FIGS. 3, 5, and 6, the clamping mechanism of the intake part 2 consist of a sleeve-shaped collet chuck 5 that is positioned so that it can slide axially in the housing 3 of the intake part and which essentially coaxially surrounds the cylindrical component 1 that is to be affixed, as well as of a slider 6 that is positioned diagonally to the cylindrical component 1 so that it can slide in the housing 3 of the intake part 2, where the collet chuck 5 and slider 6 are coupled to one another by a mortise-and-tenon control 7. This mortise-and-tenon control 7 in the illustrated embodiment consists of two control mortises 8 that are mounted on the collet chuck 5 and are each positioned in guide tracks 9 configured in the slider 6, where the guide tracks 9 seen from the axial direction of the cylindrical component 1 include a height offset.

The collet chuck 5 in turn consists of a flattened oval base body 5a, from which several fingers 5b separated from one another by crevices 10 extend outward in the axial direction to coaxially surround the cylindrical component 1 that is to be affixed. The fingers 5b separated from one another thus form a radially deformable spring element, by which a surface pressure can be exerted on the cylindrical component 1 that is to be affixed. The flattened oval—that is, non-round—configuration of the base body 5a serves to guide the collet chuck 5 in the slider 6, so that the collet chuck 5 is mounted firmly against rotation in the slider 6 by the flattened sides of the flattened oval base body 5a in such a way that the control pins 8 cannot slip out of their assigned guide tracks 9.

Figure 7:
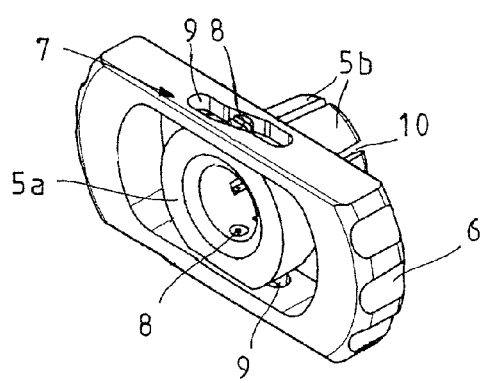
FIG. 7 shows a perspective view of the clamping part of the inventive clamping device.

The precise structure of the slider 6 as well as of the collet chuck 5 can be seen in particular from the depictions in FIGS. 6 and 7. For configuring the clamping by means of the collet chuck 5, on said collet chuck 5 a cone 11 is configured which can be brought into active connection with a counter-cone 12 configured in the housing 3 of the intake part 2. In the illustrated embodiment of the clamping device, the outer sides of the fingers 5b of the collet chuck 5 form the cone 11, while the corresponding counter-cone 12 is configured on the inner surface of the cover cap 4.

In order, first, to facilitate the installation of the intake part 2 and, second, to ensure correct insertion of the slider 6 in the housing 3, on the slider 6 and on the housing 3 of the intake part 2, mutually corresponding guide and positioning elements 13 are provided which are configured as slot-and-key connections in the embodiment illustrated in FIGS. 3 and 5. As can also be seen from FIGS. 3, 5, and 6, a securing element 14 configured as a snap ring is positioned in the housing 3 and, with the cover cap 4 removed, is intended to prevent the slider 5 from falling out of the housing 3.

To insulate the washing circuit of the medical instrument when the instrument is affixed, insulating elements 15 are positioned in the housing 3 which in the illustrated embodiment are positioned below the slider 6 in the housing 3.

Operation of the device constructed as explained above for affixing medical instruments to cylindrical components 1 proceeds as follows;

At the start of the application, the cylindrical component 1 with a free end to the front is inserted into the intake part 2 and the outer tube 2a of the clamping device, and then assumes the position shown in FIG. 1. In the depiction in FIG. 1 the component that can be affixed as a cylindrical component 1 configured as an instrument shaft is a coupling element equipped with a washing connection 16 by which the at least one additional instrument can be coupled with the instrument shaft.

Before the intake part 2 is pushed onto the cylindrical component 1 and then immediately thereafter, the clamping device is in the open position shown in FIGS. 2 and 3, in which position the intake part is positioned on the cylindrical component 1 so that it can be freely slid in the axial direction and can also be rotated around the longitudinal axis. In this open position, the control mortises 8 of the mortise-and-tenon control 7 are in the lower position in the respective guide track 9 as shown in FIG. 2.

As can be seen in the appended sectional illustration of FIG. 3, when the collet chuck 5 is in this open position above the fingers 5b of the collet chuck 5, a free space 17 is configured between the upper edge of the cover cap 4 and the free ends of the fingers 5b. The configuration of this free space 17 signifies that the cone 11 of the collet chuck 5 was not yet inserted entirely, and consequently not yet clamping, in the counter-cone 12 of the cover cap 4. For clamping affixing of the intake part 2 on the cylindrical component 1, in the subsequent working step the slider 6, proceeding from the right-hand open position illustrated in FIG. 2, is pushed into the left-hand position shown in FIG. 4 which constitutes the camping position.

Because of the coupling of the slider 6 and the collet chuck 5 by the mortise-and-tenon control 7, this pushing of the slider 6 essentially diagonally to the axial position of the cylindrical component 1 causes a lifting of the control mortises 8 into the upper position shown in FIG. 4 of the guide track 9. Because the control mortises 8 are firmly coupled with the collet chuck 5, this raising of the control mortises 8 inevitably also causes an axial sliding of the collet chuck 5 in the direction of the cover cap 4.

As can be seen from the appended sectional view of FIG. 5, in this clamping position of the collet chuck 5 above the fingers 5b of the collet chuck, just about no free space 17 more is configured between the upper edge of the cover cap 4 and the free ends of the fingers 5b. This means that the cone 11 of the collet chuck 5 was now inserted completely and therefore so that it clamps in the counter-cone 12 of the cover cap 4. Because of the lateral pressure exerted by the counter-cone 12 onto the fingers 5b of the control chuck 5, the spring-elastic fingers 5b are pressed essentially radially inward, so that the collet chuck 5 now grips the cylindrical component 1 by clamping and affixes the clamping device onto the cylindrical component so that it is stationary and secure against rotation. The clamping device is released in reverse sequence by pushing the slider 6 out of the left-hand clamping position illustrated in FIG. 5 into the right-hand open position shown in FIG. 3

This pushing of the slider 6 now causes a lowering of the control mortises 8 of the mortise-and-tenon control 7 back into the lower position in the respective guide track 9. The lowering of the control mortises 8 in turn causes an axial sliding of the collet chuck 5 away from the cover cap 4 and thus a separation of the clamping position of the cone 11 of the collet chuck 5 to the counter-cone 12 of the cover cap 4.

The intake part 2 of the clamping device is now once again positioned so that it can move freely on the cylindrical component 1 and can be withdrawn from the cylindrical component 1 by a free end.

A clamping device of this configuration is distinguished in that it can be secured at any desired point on the cylindrical component 1 so that it is stationary and secure against rotation and the clamping force exerted on the cylindrical component 1 is distributed over the circumference of the cylindrical component 1 by the configuration of an axially extending surface pressure in such a way that no in-pressing or constricting local clamping can occur.

What is claimed is:

1. A device for affixing to cylindrical components of medical instruments with at least one intake part that can be appended to the cylindrical component and secured to the cylindrical component, wherein in the intake part a sleeve-shaped collet chuck that essentially coaxially surrounds the cylindrical component is positioned, whose inner diameter can be displaced between a span that can be pushed along the cylindrical component and a span that is essentially in form-locking contiguity with the cylindrical component, characterized in that the inner diameter of the collet chuck can be displaced by a slider that can slide essentially transverse to a longitudinal axis of the cylindrical component and is mounted in the housing of the intake part;

wherein the collet chuck and the slider are in active connection with one another by means of a mortise-and-tenon control; and, wherein the mortise-and-tenon control consists of at least one control mortise that is positioned on the collet chuck and engages in a guide track configured in the slider.

2. A device according to claim 1, characterized in that mutually corresponding guide and positioning elements are provided on the slider and on the housing of the intake part.

3. A device according to claim 2, characterized in that the collet chuck and the slider are in active connection with one another by means of a mortise-and-tenon control.

4. A device according to claim 1, characterized in that a height offset is configured, looking in the axial direction of the cylindrical component, in the guide track configured in the slider.

5. A device according to claim 1, characterized in that the collet chuck is positioned so that it can slide axially in the housing of the intake part.

6. A device according to claim 1, characterized in that a cone is configured on the collet chuck and can be brought into active connection with a counter-cone configured in the housing of the intake part.

7. A device according to claim 6, characterized in that the collet chuck can slide axially by means of at least one control mortise mounted in the guide track of the slider in such a way that the cone of the collet chuck can be transferred between a position that is contiguous against the counter-cone of the housing and a position that releases the counter-cone of the housing.

8. A device according to claim 7, characterized in that the counter-cone is configured on the inside of a cover cap that can be placed on the housing of the intake part.

9. A device according to claim 6, characterized in that the counter-cone is configured on the inside of a cover cap that can be placed on the housing of the intake part.

10. A device according to claim 1, characterized in that a securing element for axial securing of the slider is positioned in the housing of the intake part.

11. A device according to claim 10, characterized in that the securing element for axial securing of the slider is configured as a snap ring.

12. A device according to claim 1, characterized in that at least one insulating element is positioned in the housing of the intake part.

13. A device according to claim 1, characterized in that the cylindrical component of the medical instrument is an instrument shaft.

* * * * *